United States Patent
Bogosian et al.

(10) Patent No.: US 6,218,145 B1
(45) Date of Patent: Apr. 17, 2001

(54) BACTERIAL EXPRESSION SYSTEMS BASED ON PLASTIC OR MITOCHONDRIAL PROMOTER COMBINATIONS

(75) Inventors: Gregg Bogosian, Chesterfield; Julia P. O'Neil, St. Louis; Jeffrey M. Staub, Wildwood, all of MO (US)

(73) Assignee: Monsanto Company, St. Louis, MO (US)

(*) Notice: Subject to any disclaimer, the term of this patent is extended or adjusted under 35 U.S.C. 154(b) by 0 days.

(21) Appl. No.: 09/283,419

(22) Filed: Apr. 1, 1999

Related U.S. Application Data

(60) Provisional application No. 60/080,432, filed on Apr. 2, 1998.

(51) Int. Cl.[7] ........................................ C12P 21/02
(52) U.S. Cl. .................. 435/69.1; 435/320.1; 435/325; 435/252.33; 435/410; 435/476; 435/194; 435/483; 435/485
(58) Field of Search .................. 435/320.1, 69.1, 435/325, 252.33, 410, 476, 194, 483, 485

(56) References Cited

U.S. PATENT DOCUMENTS

| | | | |
|---|---|---|---|
| 4,704,362 | 11/1987 | Itakura et al. | 435/253 |
| 5,221,619 | 6/1993 | Itakura et al. | 435/69.4 |
| 5,583,013 | 12/1996 | Itakura et al. | 435/69.4 |

OTHER PUBLICATIONS

Binder, Stefan et al. (1996) "Regulation of gene expression in plant mitochondria," *Plant Mol. Biol.* 32:303–314.

Hajdukiewicz, Peter et al. (1997) "The two RNA polymerases encoded by the nuclear and the plastid compartments transcribe distinct groups of genes in tobacco plastids," *EMBO J* 16:4041–4048.

Makrides, Savvas C. (1996) "Strategies for Achieving High–Level Expression of Genes in *Escherichia coli*," *Microbiological Reviews* 60:512–538.

*Primary Examiner*—James Ketter
(74) *Attorney, Agent, or Firm*—George R. Beck, Esq.; Howrey Simon; Arnold & White LLP

(57) ABSTRACT

A composition for expression of a protein-encoding gene in a host cell is described, making use of an heterologous regulon. This composition provides a protein-encoding gene under control of a promoter heterologous to the host cell, and a gene for an RNA polymerase, preferably a single-subunit RNA polymerase that recognizes the promoter heterologous to the host cell. The gene for the RNA polymerase is under control of an inducible promoter recognized by the host cell. Also disclosed is a method for expressing the protein-encoding gene using the composition described.

25 Claims, No Drawings

BACTERIAL EXPRESSION SYSTEMS BASED ON PLASTIC OR MITOCHONDRIAL PROMOTER COMBINATIONS

This application claims the benefit of U.S. Provisional Application Serial No. 60/080,432, filed Apr. 2, 1998.

BACKGROUND OF THE INVENTION

1. Field of the Invention

The present invention relates generally to the field of expression of desired, protein-encoding genes in a host cell. More particularly, it concerns expression of desired heterologous, e.g., mammalian, protein-encoding genes in a host cell wherein the heterologous gene is operably linked to a heterologous promoter recognized by a heterologous RNA polymerase, wherein the gene encoding the heterologous RNA polymerase is expressed in the host cell under the control of a host cell promoter. It also concerns ectopic expression in a host cell of desired native genes operably linked to a heterologous promoter recognized by a heterologous RNA polymerase, wherein the gene encoding the heterologous RNA polymerase is expressed in the host cell under the control of a host cell promoter.

2. Description of Related Art

Recombinant DNA technology allows insertion of a desired heterologous protein-encoding gene, which may also be referred to herein as a "target gene," into a host cell and subsequent expression of the gene product of the protein-encoding gene.

U.S. Pat. Nos. 4,704,362; 5,221,619; and 5,583,013 (Itakura et al.) disclose a method for expressing, in a bacterial host, proteins that are "heterologous" with respect to the host, i.e., not ordinarily produced by the host, using expression control systems that are "homologous" to the bacterial host, i.e., systems that are ordinarily produced by the bacterial host in its untransformed state. There are various reasons to provide new methods for expressing heterologous or, less commonly, homologous proteins in microbial hosts using a promoter system that is heterologous with respect to the host. However, some heterologous promoter systems that are advantageous for this purpose may not be recognized by the host's RNA polymerases and hence, without more, are not able to drive such expression. This invention provides a method for making such heterologous promoter systems useful to drive expression of such proteins in microbial and other hosts, by providing an RNA polymerase capable of recognizing the heterologous promoter.

A disadvantage of the homologous regulon system is the promoter recognized by the host RNA polymerase would be expected to drive expression of genes native to the host cell in addition to the protein-encoding gene. The presence of host gene products may decrease the purity of the target gene product and may require time-consuming and expensive steps for the removal of the host gene products. Therefore, it is desirable to have a system for expressing a protein-encoding gene in a host cell wherein the protein-encoding gene is under control of a promoter heterologous to the host cell, and as a result the protein-encoding gene can be expressed to yield greater purity of gene product. Such a system may be termed a "heterologous regulon." In a heterologous regulon system, it is necessary to provide a heterologous RNA polymerase that recognizes the promoter heterologous to the host cell and drives expression of the protein-encoding gene.

SUMMARY OF THE INVENTION

The present invention provides a vector system for expressing a protein-encoding gene in a host cell. The vector system comprises a plant organellar genomic promoter operably linked to the protein-encoding gene, and a second promoter operably linked to a gene encoding an RNA polymerase capable of recognizing said plant organellar genomic promoter. Preferably, the RNA polymerase of the vector system is heterologous to the host cell, i.e. not normally found in the host cell in the untransformed state. The RNA polymerase of the vector system may also be referred to as the "heterologous RNA polymerase." The plant organellar genomic promoter is not recognized by RNA polymerases of the host cell, but is instead recognized by the RNA polymerase of the vector system. In a preferred embodiment, the RNA polymerase of the vector system is a single-subunit RNA polymerase capable of recognizing promoters found in the genomes of plastids or plant mitochondria. In a further preferred embodiment, the heterologous RNA polymerase is under the control of an inducible promoter recognized by a host cell RNA polymerase.

In accordance with one aspect of the present invention, double-stranded DNAs (dsDNAs) comprising the plant organellar genomic promoter operably linked to the protein-encoding gene and the second promoter operably linked to the heterologous RNA polymerase gene are both present on single vector. In accordance with another aspect of the present invention, the dsDNAs comprising he plant organellar genomic promoter operably linked to the protein-encoding gene and the host cell promoter operably linked to the heterologous RNA polymerase gene are each present on separate vectors. In accordance with yet another aspect of the present invention, one of the dsDNAs comprising the plant organellar genomic promoter operably linked to the protein-encoding gene and the host cell promoter operably linked to the heterologous RNA polymerase gene is integrated into a host cell chromosome and the other dsDNA is present on a vector. In accordance with still another aspect of the present invention, both dsDNAs comprising the plant organellar genomic promoter operably linked to the protein-encoding gene and the host cell promoter operably linked to the heterologous RNA polymerase gene are integrated into a host cell chromosome.

The present invention also provides for recombinant host cells comprising dsDNAs in accordance with the above-mentioned elements. In a preferred embodiment, the recombinant host cell is a microbe. In a further preferred embodiment, the microbe in question is *Escherichia coli* strain K-12 W3110 or a derivative thereof. In accordance with still another aspect of the present invention, a method is provided for expressing a protein-encoding gene in a host cell, using the above-mentioned elements.

DETAILED DESCRIPTION OF PREFERRED EMBODIMENTS

The expression in a host cell of a protein-encoding gene which exists in dsDNA form involves transcription of messenger RNA (mRNA) from one strand of the DNA by an RNA polymerase enzyme. Subsequently the mRNA is processed, involving recognition of a region of the 3' UTR and addition of a tail of polyadenylate nucleotides to the 3' end of the mRNA by polyadenylation enzymes. Finally, the mRNA encounters ribosomes which associate to a region of the 5' UTR of the mRNA and then translocate in a 3'-ward direction along the mRNA. During translocation, amino acids are added to one another in sequence to form the polypeptide product of the protein-encoding gene.

Transcription of DNA into mRNA is regulated by a region of DNA usually referred to as the promoter. The promoter region contains a sequence of bases that signals RNA polymerase to associate with the DNA, and to initiate the transcription of mRNA using one of the DNA strands as a template to make a corresponding complementary strand of RNA. RNA polymerases from different species typically recognize different sequences of bases as promoter regions. In order to express a protein-encoding gene in a host cell, either the promoter driving transcription of the protein-encoding gene must be recognized by a host RNA polymerase, or an RNA polymerase which recognizes the promoter driving transcription of the protein-encoding gene must be provided to the host cell.

Most work in the field has focused on expression systems in which the promoter driving transcription of the protein-encoding gene is replaced with one recognized by host RNA polymerase. An example of such a system is the homologous regulon disclosed by U.S. Pat. Nos. 4,704,362; 5,221,619; and 5,583,013 (Itakura et al.). The approach of the present invention is to import into the host cell both a protein-encoding gene under control of a heterologous promoter and a gene or genes encoding a heterologous RNA polymerase that recognizes the heterologous promoter. The gene or genes for the heterologous RNA polymerase must be under control of a promoter recognized by a host RNA polymerase.

RNA polymerases which are known or are found to cause transcription from promoters heterologous to host cells can be used in the present invention. Typical host cells include, but are not limited to, bacteria, fungi, plant cells, and animal cells. Typical RNA polymerases and the promoters they recognize can be obtained from a variety of sources, including but not limited to animals, animal organelles, animal viruses, plants, plant organelles, plant viruses, and bacterial viruses. It is preferred that the RNA polymerase selected should be capable of causing high expression of the protein-encoding gene so as to substantially increase the percentage of target gene product in total host cell protein. It is further preferred that the RNA polymerase selected is comprised of a single protein species, i.e. the RNA polymerase is a single-subunit RNA polymerase. The single protein species can be present in more than one copy per active RNA polymerase, e.g in the active form the RNA polymerase can be a homomonomer, homodimer, homotrimer, homotetramer, etc. An RNA polymerase comprised of a single protein species is advantageous because it requires only one host promoter::heterologous RNA polymerase gene construct to be inserted into the host cell, instead of multiple constructs. Further advantages of a single subunit RNA polymerase are, first, no need for expression of stoichiometric levels of multiple subunits when only one subunit goes into the RNA polymerase, and second, a reduced likelihood of mismultimerization when only one subunit is matched against the panel of host cell proteins.

Several RNA polymerases are known that comprise a single subunit. Among these are RNA polymerases encoded by the genomes of bacteriophages such as T3 and T7, and RNA polymerases encoded by genes in plant nuclei and driving expression of genes in the genomes of plastids and plant mitochondria. Although plastid- and plant-mitochondria-active plant-nuclei-encoded single-subunit RNA polymerases (hereinafter, "plant plastid RNA polymerases" or "plant mitochondrial RNA polymerases") have been termed "phage-like," it is hereby reported that T7 RNA polymerase does not recognize plastid promoters. Such lack of functional homology will herein delineate bacteriophage RNA polymerases from plant plastid or mitochondrial RNA polymerases.

The plant plastid or mitochondrial RNA polymerases encoded by plant nuclear genomes are distinct from RNA polymerases encoded by genes in plastid genomes; plastid-encoded RNA polymerases are multi-subunit and recognize promoters similar to those recognized by native E. coli RNA polymerases, whereas promoters recognized by single-subunit plant RNA polymerases are commonly not similar to those recognized by native E. coli RNA polymerases.

Plastids and mitochondria are two types of organelles commonly found in plant cells. Mitochondria provide energy for the cell in the form of adenosine triphosphate (ATP), whereas plastids can perform several different functions. In green tissues, many plastids have differentiated to form chloroplasts, organelles that perform photosynthesis. Both plastids and mitochondria have their own genomes, distinct from both the plant cell nuclear genome and the other organellar genome. Though not to be limited by theory, it is widely hypothesized that plastids and mitochondria were originally free-living prokaryotic organisms that evolved a symbiotic relationship with progenitors of contemporary plants. The first ancestors of contemporary plastids and plant mitochondria to live in symbiosis with plants presumably had complete prokaryotic genomes suitable for existence as free-living organisms. Within the cytoplasm of a plant cell, however, many of the genes needed by the free-living ancestors of plastids and plant mitochondria were dispensable, and have subsequently been deleted from the plastid and plant mitochondrial genomes. However, not all genes now missing from the organellar genomes have been lost. Some genes have been transferred from the organellar genomes to the plant nuclear genome. Examples of such transferred genes include the plastid and mitochondrial single-subunit RNA polymerases. As a result of the deletion and export of genes from the plastid and plant mitochondrial genomes, plastids and plant mitochondria are incapable of survival and propagation independent of the plant cell, and must therefore be viewed as part of the plant cell.

Definitions

The following definitions will serve to clarify terms used herein. Terms not expressly defined will have definitions implied by their uses herein.

"Protein-encoding gene," as used herein, refers to a gene which is desired to be expressed in a host cell. A protein-encoding gene will be used as a double-stranded DNA molecule unless otherwise specified. A protein-encoding gene may also be referred to herein as a "target gene." Typically, the protein-encoding gene will be heterologous to the host cell. However, the protein-encoding gene can be native to the host cell, but its expression may be desired under conditions different than those under which it is normally expressed or to levels greater or less than those to which it is normally expressed. Expression of a protein-encoding gene native to the host cell under conditions or to levels not normally observed in the host cell will herein be termed "ectopic expression." Examples of protein-encoding genes that can be used in the present invention include, but are not limited to, bovine somatotropin, porcine somatotropin, and human somatotropin.

A "host cell," as used herein, refers to a cell in which a protein-encoding gene is desired to be expressed. Preferably, a host cell is readily transformed with heterologous DNA and will transmit the heterologous DNA to progeny with an acceptably low failure rate. A host cell can be a microbe (as defined below); a plant cell cultured in embryo, callus, or differentiated tissue such as leaf, root, or stem of a mature plant; or an animal cell, either grown in tissue culture or found in differentiated tissue of a mature animal. One of skill in the art will be aware of numerous cells that can be useful as host cells in the present invention. Preferably, the host cell is a microbe.

"Heterologous," as used herein, describes a molecule present in a host cell in which it is not normally found in the natural state. For example, when *Escherichia coli* is a host cell of the present invention, then an RNA polymerase provided to *E. coli* which is different in sequence from any normally found in *E. coli*, and normally non-functional in *E. coli*, is a heterologous RNA polymerase. Similarly, a DNA molecule encoding the above RNA polymerase is a heterologous DNA.

"Microbe" and "microbial," as used herein, refer to a unicellular microorganism suitable for use in the present invention. A unicellular microorganism is suitable for use in the present invention if it can be transformed with heterologous DNA and subsequently cultured with an acceptably low rate of failure to transmit the heterologous DNA to its progeny. A microbe containing heterologous DNA may herein be termed a "recombinant microbe." Progeny cells of a recombinant microbe, though also recombinant microbes, may be referred to distinctly as "daughter cells." Both prokaryotic and eukaryotic single-cell microorganisms can be used, including, but not limited to, members of prokaryotic genera such as Escherichia, Bacillus, and Pseudomonas, and eukaryotic genera such as Chlamydomonas and Saccharomyces. One of skill in the art will be aware of numerous microbes that can be used in the present invention.

"Vector," as used herein, refers to any DNA molecule suitable for cloning of any or all of a protein-encoding gene, a heterologous RNA polymerase gene, and operably-linked promoters, and/or transformation of a host cell. Examples of vectors that can be used in the present invention include plasmids, cosmids, phagemids, and yeast artificial chromosomes, among others. A vector containing at least one of the heterologous promoter::protein-encoding gene or host cell promoter::heterologous RNA polymerase gene constructs may be referred to as a "recombinant vector." One of skill in the art will be aware of various vectors that can be used in the present invention.

A "vector system," as used herein, refers to any vector or combination of vectors comprising all of a protein-encoding gene, a heterologous RNA polymerase gene, and operably-linked promoters. In one embodiment, the heterologous promoter::protein-encoding gene are present on a first vector and the host cell promoter::RNA polymerase gene are present on a second vector. In a second embodiment, both the heterologous promoter::protein-encoding gene construct and the host cell promoter::RNA polymerase gene construct are present on a vector.

"Inducible promoter," as used herein, refers to a promoter activatable by addition of a particular molecule, called an inducer, to a medium containing cells comprising the inducible promoter. Such an inducer may be said to be "corresponding" to the inducible promoter. Those of skill in the art will be aware of inducers corresponding to known inducible promoters that can be used in the present invention. The mode of action of an inducer involves uptake of the inducer by the cells and association of the inducer with protein factors. Association of the inducer leads, directly or indirectly, to the association of RNA polymerases to the inducible promoter at levels much greater than obtained previously.

"Promoter," as used herein, refers to a sequence of DNA which directs transcription of an operably linked gene. The term "promoter" will refer to a double-stranded DNA unless otherwise specified. RNA polymerases associate to the promoter, and then generate transcripts of the gene operably linked to the promoter. RNA polymerases are only capable of associating to promoters that have a specific sequence of bases recognized by the RNA polymerase. An RNA polymerase that can bind to the specific sequence of the promoter may be said to be "capable of recognizing" the promoter. RNA polymerase can only generate transcripts of a gene operably linked to the promoter if the RNA polymerase is capable of recognizing the promoter.

"Operably linked," as used herein, refers to a state of joinder of a promoter and a gene, wherein RNA polymerases that are capable of recognizing the promoter can then generate transcripts of the gene.

"Plant organellar genomic promoter," as used herein, refers to a promoter normally found only in the genomic DNA of plastids or plant mitochondria, capable of directing transcription of an operably linked gene.

A "plant RNA polymerase," as used herein, will refer to any RNA polymerase encoded by a gene normally found in the genomic DNA of a plant. Specific plant species that can be the source of the plant RNA polymerase include, but are not limited to, *Arabidopsis thaliana* and *Nicotiana tabacum*. The genomic DNA may be found in either the nuclear genome, the plastid genome, or the mitochondrial genome.

A "plant plastid RNA polymerase," as used herein, will refer to a single-subunit RNA polymerase encoded by a gene found in the nuclear genome of a plant, and capable of recognizing a promoter or promoters found in the plastid genome of the plant. Specific plant species that can be the source of the plant plastid RNA polymerase include, but are not limited to, *Arabidopsis thaliana* and *Nicotiana tabacum*. The genes encoding any RNA polymerase described herein will be present as double-stranded DNA unless otherwise specified.

"Gene product," as used herein, refers to the polypeptide produced by transcription of a specific DNA coding region into mRNA followed by translation of the mRNA by a ribosome. Such a polypeptide may also be referred to as a "protein." If the gene product functions as a catalyst in a chemical reaction, the gene product may also be referred to as an "enzyme."

Protein-encoding Genes

Any desired gene can be used as a protein-encoding gene according to the present invention. The protein-encoding gene can either be cloned from a genomic DNA library or a cDNA library, or synthesized if the nucleotide sequence is known. Techniques for cloning and subcloning DNA and generating genomic DNA and cDNA libraries are widely known to those of skill in the art, and oligonucleotide synthesis can be performed by any of several commercially available synthesizers known to those skilled in the art. Although any gene product can be produced using the compositions and methods of the present invention, the most convenient purifications will be possible if the gene product has characteristics distinct from those of the native gene products of the host cell. Examples of such characteristics include, but are not limited to, molecular weight, net charge, isoelectric point, solubility as a function of ammonium sulfate concentration, heat lability, pH lability, and sensitivity to chaotropic agents such as urea or guanidinium chloride. Any such limitations on convenience of purification are shared with all other known systems for expressing protein-encoding genes in host cells.

In all embodiments of the present invention, the protein-encoding gene must be placed under control of a heterologous promoter, the promoter being recognizable by the heterologous RNA polymerase. If the protein-encoding gene is isolated from a plastid or plant mitochondrion genomic library, no modification may be required if the protein-encoding gene is one naturally under control of a promoter recognized by the heterologous RNA polymerase intended to be used. Similarly, if a multiple-subunit RNA polymerase is intended to be used, and the protein-encoding gene in the native state is operably linked to a promoter recognized by the multiple-subunit RNA polymerase and is isolated with the promoter intact, no modification may be required.

In many cases, however, the protein-encoding gene cannot be isolated with a promoter recognizable by the heterologous RNA polymerase intended to be used. This can happen when the protein-encoding gene is isolated from a cDNA library, isolated from a genomic library of an organism that does not provide a heterologous RNA polymerase intended to be used, or for other reasons. The protein-encoding gene must then be operably linked with a usable promoter, a promoter recognizable by the heterologous RNA polymerase intended to be used.

If the protein-encoding gene is operably linked to a non-usable promoter, several techniques exist by which the non-usable promoter can be replaced by a usable promoter. If the sequence of the non-usable promoter differs by only a few nucleotides from that of the usable promoter, site-specific mutagenesis can be performed on the non-usable promoter to alter its sequence and turn it into the usable promoter. Techniques for site-specific mutagenesis of either single stranded DNA (ssDNA) or dsDNA forms of a vector are well-known to one of skill in the art, and are available in kit form from various suppliers, as is well known to those skilled in the art.

If the non-usable promoter differs greatly in sequence from a usable promoter, replacement of the non-usable promoter can be more readily effected by excision of the non-usable promoter and insertion of a usable promoter, a technique commonly referred to as cassette mutagenesis. If, in the dsDNA vector, the non-usable promoter is flanked by restriction enzyme sites, the vector can be cut with the appropriate restriction enzyme or enzymes, the fragment of dsDNA comprising the non-usable promoter can be separated from the remainder of the vector including the protein-encoding gene, and a second fragment of dsDNA comprising a usable promoter and overlapping ends complementary to the overlapping ends of the remainder of the vector can be annealed to the remainder of the vector. The remainder of the vector and the second fragment of dsDNA can then be linked 3'-5' by treatment with ligase. The second fragment of dsDNA, comprising the usable promoter, can be either synthesized if the sequence is known or subcloned from an isolated usable promoter. Techniques and equipment for restriction enzyme digestion, separation of dsDNA fragments based on size, annealing of two DNA molecules with complementary overlapping ends, ligation, oligonucleotide synthesis, and subcloning are widely known and readily available to those of skill in the art.

In other cases, the non-usable promoter cannot be flanked by restriction enzyme sites. As a result, excision of the non-usable promoter as outlined above requires construction of a flanking restriction enzyme site or sites using site-specific mutagenesis techniques as described above.

In some situations, it may not be necessary to excise the non-usable promoter. Instead, if a restriction enzyme site is found or constructed between the non-usable promoter and the protein-encoding gene, and the recombinant vector is cut with the appropriate restriction enzyme, a dsDNA fragment comprising a usable promoter with complementary overlapping ends can be annealed to the recombinant vector and ligated to operably link the usable promoter with the protein-encoding gene. The techniques to be used are as described above. Because both ends of the fragment comprising the usable promoter are identical, the fragment can insert into the vector in either the operably-linked or the non-operably-linked orientation. The orientation of a vector can be checked by sequencing, in vitro translation, or other techniques, all of which are widely known to those of skill in the art.

Optimization of production of the gene product may require modification of any or all of the coding region, the 5' UTR, and the 3' UTR. In the coding region, the nucleotide sequence of the protein-encoding gene can be kept the same as that of the wild-type gene found in the genome of the source organism, or it can be different. Owing to the degeneracy of the genetic code, changes in the nucleotide sequence of the protein-encoding gene need not necessarily lead to changes in the amino acid sequence of the gene product.

For example, the nucleotide sequence of the coding region of the protein-encoding gene can be altered to remove or insert restriction enzyme sites. Removal of a restriction enzyme site or sites can be needed for successful transformation of restriction-positive prokaryotic hosts which express the corresponding restriction enzyme; however, it is preferred, when using prokaryotic hosts, to use prokaryote hosts that are restriction-minus. Insertion of restriction enzyme sites may be desired to allow convenient cassette mutagenesis of particular regions of the coding sequence. Removal or insertion of restriction enzyme sites can be affected by site-specific mutagenesis or cassette mutagenesis techniques as described above.

If the protein-encoding gene is of eukaryotic origin and is isolated from genomic DNA, not cDNA, and the host cell is a prokaryote, any introns present in the coding region of the protein-encoding gene must be removed. Prokaryotes lack enzymes capable of recognizing introns and splicing them from RNAs. Removal of introns from a protein-encoding gene can be performed by addition of restriction enzyme sites at positions immediately adjacent the ends of the introns, followed by excision and reannealing, all of which techniques are widely known to those of skill in the art. Alternatively, the protein-encoding gene can be expressed in vivo in a eukaryotic organism, the mRNAs isolated from the eukaryote, a set of cDNAs made by treating the mRNAs with reverse transcriptase, the cDNAs cloned into a DNA construct for the purpose of forming a cDNA library, and the cDNA library screened with portions of the protein-encoding gene to find a cDNA which is a dsDNA version of the protein-encoding gene without introns. Techniques required to construct and screen cDNA libraries are well known to those of skill in the art.

Modifications to the codon usage of the coding sequence of the protein-encoding gene can also be helpful to optimize expression of the protein-encoding gene. Although codon usage is not widely believed to impact the translational efficiency of an mRNA in higher eukaryotes, a codon bias similar to that of *E. coli* does enhance the translational efficiency of heterologous genes in *E. coli*. Avoidance of infrequently-used codons can also lead to enhanced stability of an mRNA, as sequences that promote instability of mRNAs often comprise infrequently-used codons. Sequences that promote instability of mRNAs can also be avoided in and of themselves. Any of these changes, and all others not described, can be readily performed using techniques widely known to those of skill in the art.

As described above, due to the degeneracy of the genetic code, nucleotide changes in the coding region do not automatically lead to changes in the amino acid sequence. However, the amino acid sequence of the protein product can be changed by changing the nucleotide sequence of the protein-encoding gene by techniques described above.

It can be desirable to alter the stability of the protein by alterations in the coding sequence of the protein-encoding gene. Often, it is desired to enhance the stability of the protein in order to minimize its rate of degradation and increase the level of the protein present in the host cell. In certain situations, for example, in preparing a protein for experiments in which the dependence of a phenotypic effect on the stability of a protein is to be examined, it can be desired to diminish the stability of the protein. In either case, specific amino acids of the gene product can be added, deleted, or substituted to alter the stability of the protein with minimal alteration of other properties by alteration of the nucleotide sequence of the coding region of the protein-encoding gene.

Also, it can be desirable to alter the enzymatic activity of the protein by changing the nucleotide sequence of the coding region of the protein-encoding gene. As described above, the new enzymatic activity can be enhanced or diminished relative to the old. Similarly, the nucleotide sequence of the coding region of the protein-encoding gene can be altered to add target peptides or signal peptides to the protein. Such target peptides or signal peptides can direct the protein to a specific organelle, to a cell membrane, or to be secreted. The amino acid sequence of the protein can also be altered for reasons not enumerated here. Any protein-encoding gene, with or without changes in the nucleotide sequence of its coding region, that can be constructed by techniques known to the art can be used in an expression system or method of the present invention.

The 5' and 3' untranslated regions (UTRs) of the protein-encoding gene transcript can also be cloned or synthesized, and in either case changed or left intact, by techniques referred to above.

The 5' UTR comprises the ribosome binding site, and also plays a role in mRNA stability. It is widely known that ribosome binding sites from eukaryotes are non-functional in prokaryotes, and vice versa. Use of a ribosome binding site dissimilar to the consensus sequence for ribosome binding sites in the host cell can lead to either reduced rates of translation of the gene product, recognition of cryptic ribosome binding sites elsewhere in the mRNA with subsequent translation of non-desired truncated or frame-shifted proteins, or both. To avoid such unwanted effects, the ribosome binding site of the 5' UTR of the protein-encoding gene can be modified from its native or original sequence to match or nearly match the consensus sequence for the ribosome binding site in the host cell. Such modification can be affected by site-specific mutagenesis or cassette mutagenesis techniques as described above. Also, specific sequences in the 5' UTR can enhance or diminish the stability of the mRNA depending on the host cell, and stabilizing sequences can be added and destabilizing sequences removed by the site-specific mutagenesis or cassette mutagenesis techniques as described above. 5' UTR stabilizing and destabilizing sequences in particular host cells are widely know to those of skill in the art.

The 3' UTR plays a role in mRNA stability. During eukaryotic mRNA processing, an AT-rich sequence in the 3' UTR is recognized by protein factors. These proteins splice the mRNA at a nearby location in the 3' UTR and add a tail consisting of adenine nucleotides, usually referred to as the poly(A)+tail. Addition of the poly(A)+tail increases the half-life of an mRNA.

It is well known that the prokaryotic 3' UTRs are generally non-functional in eukaryotes, and vice versa. Determination of any modifications needed to make the 3' UTR of the protein-encoding gene functional in the intended host will be routine to one of skill in the art. Modifications of the 3' UTR of the protein-encoding gene can be made by site-specific mutagenesis or cassette mutagenesis techniques described above.

Plant Organellar Genomic Promoters

Any promoter recognized by an RNA polymerase heterologous to the host cell can be used in the present invention as a promoter to drive expression of the protein-encoding gene. In an embodiment of the present invention, the promoter recognized by an RNA polymerase heterologous to the host cell will not be recognized by any RNA polymerase normally found in the host cell, in order that protein-encoding genes operably linked to that promoter are not expressed in significant proportion without the activity of the RNA polymerase heterologous to the host cell.

Also, it is preferred that the heterologous promoter will be recognized by a heterologous single-subunit RNA polymerase, for reasons that will be discussed below. This preferred embodiment requires that the heterologous promoter be a plant organellar genomic promoter. The plant organellar genomic promoter can be either one known to those of skill in the art (e.g., previously reported to a nucleic acid sequence databank such as GenBank) or can be one isolated by techniques widely known to those of skill in the art. One method of isolating a promoter is by forming DNA constructs in which putative promoter regions are operably linked each to its own copy of a reporter gene, for example β-glucuronidase (GUS), green fluorescent protein (GFP), or luciferase; transforming a host cell or organelle with the DNA construct; and assaying for the production of GUS, GFP, or luciferase gene products by techniques specific to each reporter gene and widely known to those of skill in the art. High levels of reporter gene product indicate the putative promoter is recognized by an RNA polymerase present in the host cell or organelle. Alternatively, the reporter gene product can be detected by enzyme-linked immunosorbent assay (ELISA), an assay widely known in the art. Another alternative is in vitro expression using the DNA construct, the RNA polymerase of interest, ribosomes, and other factors. The factors needed and techniques for performing in vitro expression are widely known to those of skill in the art. A further method of isolating promoters is mapping of transcripts in vivo. Plant organellar genomic promoters, and more widely, heterologous promoters, selected by any method can be used in the compositions and methods of the present invention.

Preferably, a plant organellar genomic promoter can drive a high rate of transcription of a gene under its control in conjunction with the appropriate heterologous RNA polymerase, in order to maximize expression of the protein. The position of the promoter relative to the intended transcription start site is most preferably the same as in the organism that is the source of the RNA polymerase. Techniques for providing the protein-encoding gene with the plant organellar genomic promoter at the preferred orientation and distance have been described above.

A plant mitochondrial promoter can be used as plant organellar genomic promoters in the present invention. Consensus sequences for mitochondrial promoters of wheat, maize, and dicots have been recently reported by Binder et al., Plant Molecular Biology, Vol 32, pp. 303–314, 1996, which is hereby incorporated by reference in its entirety.

Plastid promoters can be used as plant organellar genomic promoters in the present invention. Most plastid genes contain a promoter for the multi-subunit plastid-encoded RNA polymerase (PEP) as well as the single-subunit nuclear-encoded RNA polymerase. A consensus sequence for the nuclear-encoded polymerase (NEP) promoters and listing of specific promoter sequences for several native plastid genes can be found in Hajdukiewicz et al., 1997, EMBO J. Vol. 16 pp. 4041–4048, which is hereby in its entirety incorporated by reference.

A plastid promoter that can be used as a plant organellar genomic promoter of the present invention is the Zea mays plastid RRN (ZMRRN) promoter (SEQ ID NO:1). As will be described in the examples, the ZMRRN promoter was shown to not drive expression of a reporter gene in E. coli, but is expected to drive expression of a reporter gene in E. coli strain K-12 W3110 in the presence of Arabidopsis thaliana plastid RNA polymerase. Similar promoters that can be used in the present invention are the Glycine max plastid RRN (SOYRRN) and the Nicotiana tabacum plastid RRN (NTRRN) promoters (SEQ ID NO:2 and SEQ ID NO:3, respectively). All three promoters can be recognized by the Arabidopsis plastid RNA polymerase. The general features of RRN promoters are described by Hajdukiewicz et al.

RNA Polymerases Capable of Recognizing Plant Organellar Genomic Promoters

Any RNA polymerase that is heterologous to the host cell can be used as a heterologous RNA polymerase of the present invention. Preferably, the RNA polymerase is a single subunit RNA polymerase, more preferably a plastid- or plant-mitochondria-active single subunit RNA polymerase capable of recognizing a plant organellar genomic promoter. Although the only known plastid- or plant-mitochondria-active single subunit RNA polymerases are encoded by plant nuclear genes, any such single-subunit RNA polymerases subsequently found to by encoded by a plant organellar genome can be used in the present invention. New single-subunit RNA polymerase genes can be isolated from genomic DNA or cDNA libraries by a variety of methods widely known to those of skill in the art. In one method, an oligonucleotide probe derived from the nucleotide sequence of a known single subunit RNA polymerase gene is used to screen a library for genes with partial or complete sequence similarity by low-stringency or high-stringency hybridization. Techniques for performing the above method are widely known in the art. In another method, a novel single subunit RNA polymerase is purified, all or part of its amino acid sequence determined, and a set of degenerate oligonucleotides prepared for probing a library as described above. Other methods are known to those of skill in the art, and can be used to isolate single subunit RNA polymerase genes useful in the present invention.

A single subunit RNA polymerase gene can be modified, with similarities in scope, intent, and technique to the modifications described under "Protein-encoding genes" above. The RNA polymerase gene must be placed under control of a host cell promoter as described below. The coding region of the RNA polymerase gene can be modified to have a codon usage more closely resembling that of the intended host cell, in order to increase the rate of translation and remove destabilizing sequences. Destabilizing sequences in the coding region of the RNA polymerase gene per se can be removed. The amino acid sequence of the RNA polymerase can undergo additions, deletions, and/or substitutions by altering the nucleotide sequence of the coding region of the RNA polymerase gene, in order to enhance the stability and/or increase the rate and/or accuracy of transcription of the RNA polymerase. The 5' UTR of the RNA polymerase gene can be modified to provide a ribosome binding site more readily recognized by the host cell, and to enhance the stability of the mRNA. The 3' UTR of the RNA polymerase gene can be modified to enhance polyadenylation and stability of the mRNA. Techniques for performing all of the above modifications are widely known to those of skill in the art, as described above.

Single subunit RNA polymerases are preferred for use in the present invention because only one RNA polymerase gene must be prepared for expression in the host cell. Multiple subunit RNA polymerases are encoded by two or more genes, both of which would be required to be modified for expression in the host cell, expending more time and laboratory resources in the process. Single subunit RNA polymerases are also preferred for reasons discussed under "Vectors and transformation" below.

A single subunit RNA polymerase that can be used in the present invention is Arabidopsis plastid polymerase. As described in the examples, Arabidopsis plastid polymerase is believed to recognize the ZMRRN, SOYRRN, and NTRRN promoters but is not believed to amplify genes under the control of any known E. coli promoters.

Promoters for RNA Polymerase

Any promoters normally found in a host cell in the native state can be used in the present invention to drive expression of the RNA polymerase. In addition, any promoter not normally found in the host cell in the native state but that is recognized by a native or normally native host cell RNA polymerase can be used in the present invention to drive expression of the RNA polymerase. In either case, such a promoter may be referred to herein as a "second promoter." Similarly to the selection of plant organellar genomic promoters described above, either the second promoter can be selected from a nucleic acid sequence database accessible to those of skill in the art, e.g., GenBank, or the second promoter can be isolated by a screening method as described under "Plant organellar genomic promoters" above. Any promoter recognized by the host cell can be operably linked to the gene or genes encoding the heterologous RNA polymerase. The operable linkage can be constructed using any known techniques for DNA manipulation, as referred to above.

Second promoters can conveniently be described as either constitutive or inducible. Constitutive promoters are those which are always active in driving expression of genes under their control. Inducible promoters, in contrast, are only activated in response to specific environmental stimuli. Either type of promoter can be used in a system for expressing non-host genes in a host cell. Preferably, inducible promoters can be used, in order to provide greater control over the timing of expression of the RNA polymerase and subsequent expression of the protein-encoding gene. Such greater control will be described in detail below.

Inducible promoters that can be used to drive expression of the heterologous RNA polymerase, in embodiments in which the host cell is *E. coli*, include, but are not limited to, trp, tac, lac, ara, recA, λPr, and λPl. These promoters and others that can be used in the present invention for expression of the heterologous RNA polymerase in embodiments in which the host cell is *E. coli* are described by Makrides, *Microbiological Reviews*, (1996), 60, 512–538, hereby incorporated herein in its entirety by reference, and references therein.

In light of the present disclosure, other inducible promoters active in *E. coli* and widely known to those of skill in the art can be used to drive expression of the heterologous RNA polymerase in embodiments of the present invention wherein the host cell is *E. coli*.

Further, in embodiments of the present invention wherein the host cell is a microbe other than *E. coli*, for example, Saccharomyces, Bacillus, and Pseudomonas, among others, any inducible promoter known to those skilled in the art to be active in the host cell can be used to drive expression of the heterologous RNA polymerase.

Although not preferred, constitutive promoters can be used to drive expression of the heterologous RNA polymerase. Again, any constitutive promoter known to one skilled in the art to be active in a host cell of the present invention can be used to drive expression of the heterologous RNA polymerase.

Vectors and Transformation

Any vector system wherein a protein-encoding gene is present and operably linked to a heterologous promoter and a heterologous RNA polymerase capable of recognizing the heterologous promoter and transcribing the protein-encoding gene is present and operably linked to a host cell promoter can be used to transform a host cell and express the protein-encoding gene according to the present invention.

It is important that the vectors are capable of being replicated in the protein-encoding. Vectors incapable of replication in the protein-encoding will result in failure of progeny of the recombinant host to inherit the vector and subsequent failure to express the protein-encoding gene. Even if the protein-encoding gene and/or heterologous RNA polymerase gene are intended to be integrated into the host cell genome by recombination or other method known to those of skill in the art, it can be desirable to use vectors capable of replication if the time required for integration is long or if the rate of successful integration is low.

Preferably, the vectors are capable of transforming a host cell with multiple copies and/or are capable of replication at rates in excess of the rate of replication of the host cell. Either or both capabilities are preferred to give rise to recombinant hosts with large numbers of the vector or vectors. With a large number of copies of the protein-encoding gene present in the recombinant host, the rate of transcription of the protein-encoding gene will be greater than if a small number of copies of the protein-encoding gene is present, provided that sufficient active units of the heterologous RNA polymerase are present to prevent the concentration of the heterologous RNA polymerase from being rate-limiting.

Preferably, a vector for use in the present invention will comprise a gene or genes encoding a selectable marker protein. If the selectable marker protein is expressed from a gene present on the vector by a recombinant host lacking the gene encoding the selectable marker protein, the recombinant host will exhibit a phenotypic response that an identical cell not comprising the vector will not exhibit. Typically, the selectable marker protein confers resistance to an antibiotic onto the recombinant host cell, and the recombinant host cell will grow on a medium containing the antibiotic whereas an identical cell not comprising the vector will not survive on the medium. Molecular biological techniques for culturing cells on media and screening for the presence of selectable marker genes are widely known to those of skill in the art.

Any cell that can be transformed by recombinant vectors and can be screened for expression of a selectable marker can be used in the present invention. Preferably, the host cell is a microbe. Normally, a microbe can be more readily cultured by standard techniques and can grow more rapidly. Microbes suited for use in the present invention include, but are not limited to, those from the prokaryotic genera Escherichia, Bacillus, Pseudomonas, and the eukaryotic genera Saccharomyces, Chlamydomonas, Chlorella and Euglena. More preferred microbes include *E. coli* strain K-12 W3110 and derivatives thereof.

In one embodiment of a vector system of the present invention, the protein-encoding gene and the heterologous promoter to which the protein-encoding gene is operably linked are present on a first vector and the RNA polymerase gene and the host cell promoter to which the RNA polymerase gene is operably linked are present on a second vector. The vectors can be any vectors that are capable of being introduced into and replicated within the host cell. In this embodiment, it is important that the two vectors be compatible, i.e., have different origins of replication, in order to maximize co-inheritance of the two vectors by progeny cells of the recombinant host. If the vector comprising the protein-encoding gene and heterologous promoter is inherited by progeny cells of the recombinant host at a higher frequency than the vector comprising the RNA polymerase gene and host promoter is inherited, many progeny cells will arise in which the protein-encoding gene is not expressed because RNA polymerase is not present to transcribe the protein-encoding gene. Conversely, if the vector comprising the protein-encoding gene and heterologous promoter is inherited by progeny cells of the recombinant host at a lower frequency than the vector comprising the RNA polymerase gene and host promoter is inherited, many progeny cells will arise in which the protein-encoding gene is not expressed because the protein-encoding gene is not present to be transcribed by RNA polymerase.

Determining whether two known vectors are compatible involves comparing their origins of replication, and is readily performed by one of skill in the art.

In another embodiment of a vector system of the present invention, a protein-encoding gene operably linked to a heterologous promoter and a heterologous RNA polymerase gene operably linked to a host cell promoter can be present on the same vector. An advantage of this embodiment is that the heterologous RNA polymerase gene and the protein-encoding gene will always be co-inherited by progeny cells, except in rare cases of partial loss of the vector sequence. However, the vector on which both genes are present can be lost by progeny cells during reproduction. Nevertheless, nearly all of the progeny cells of the recombinant host would be expected to comprise both the protein-encoding gene and the heterologous RNA polymerase gene.

In an embodiment of a recombinant host of the present invention, the protein-encoding gene is present on a vector and the heterologous RNA polymerase gene is integrated into the host cell genome. A recombinant host of this embodiment can be transformed with any vector system describe above. After transformation, integration of the heterologous RNA polymerase gene can be effected by any known technique, e.g. integration by bacteriophage vectors or recombination from a plasmid. An advantage of this embodiment is that the heterologous RNA polymerase gene will always be inherited by progeny cells of the transformed host. The possibility remains that the vector comprising the protein-encoding gene can be lost during propagation of the progeny cells.

In a further embodiment of a recombinant host, the protein-encoding gene and the heterologous RNA polymerase gene can be both integrated into the host cell genome. This embodiment has the advantages of co-presence of both the protein-encoding gene and the heterologous RNA polymerase gene, and guaranteed inheritance of both genes by progeny cells of the transformed host.

Transformation of the host cell with the vector or vectors comprising the protein-encoding gene, the heterologous RNA polymerase, and their respective promoters, can be affected by any one of several techniques widely known to those of skill in the art. For example, in the embodiment of the present invention in which the recombinant host cell is E. coli, the microbe can be transformed with the vector system by the calcium chloride ($CaCl_2$) method. Briefly, a culture of E. coli is treated with, typically, 50 mM $CaCl_2$ in sterile water at 4° C. to permeabilize its cell walls to DNA. The vector system is then added to the culture and incubated for 30–45 min at 4° C., followed by a heat shock of 42° C. for 45–90 sec. The culture can then be plated immediately, after a further 5–15 min incubation at 4° C., or after addition of 1 mL of medium and incubation for 60 min at 37° C. Plating comprises spreading an aliquot of the putatively transformed culture on the surface of a solid agar medium containing the antibiotic or antibiotics to which the selectable marker gene or genes on the vector or vectors can grant resistance to recombinant E. coli. The plated E. coli are then incubated at 37° C. for 16 h, and only those E. coli expressing selectable marker genes granting resistance to all antibiotics present in the medium will survive and reproduce, forming distinct colonies on the plate, each colony being daughter cells of a single recombinant microbe. Techniques for transformation of host cells by other means, and transformation of other host cells, are widely known to those of skill in the art.

Culturing and Fermentation

In embodiments wherein the host cell is a microbe, in order to produce a large amount of the target gene product, it is preferred to grow up a colony of recombinant microbe in a fermentor. The size of fermentor is not critical. In order to grow up a colony of recombinant microbe, a colony is transferred from a plate to a test tube containing a liquid medium comprising additionally all antibiotics present in the plating medium. The volume of liquid in the test tube is typically 1.5–5 mL. The colony is then grown in the test tube, typically at 37° C., typically for 8–16 h, typically aerated by shaking. After growth, an aliquot is typically transferred to a larger test tube or flask containing the liquid medium comprising additionally all antibiotics present in the plating medium, typically with a liquid volume of 10–50 mL. A further growth cycle is performed, substantially the same as the first. A second transfer can be performed of an aliquot of the grown culture from second flask to a third flask containing the identical liquid medium and antibiotics, typically with a liquid volume of 100–1000 mL. A growth cycle is performed with the same parameters as the first. When all desired growing up has been performed, all or part of the contents of the final flask can be transferred to a fermentor containing the liquid medium and the antibiotic or antibiotics used previously, typically with a liquid volume of 100–1000 L. In light of the present disclosure, variations and modifications of the fermentation procedure will be clear to one skilled in the art, and any such variations and modifications are to be construed as being within the spirit and scope of the present invention.

In the fermentor, the culture is grown at controlled temperature, pH, and aeration until maximum cell density is reached. A further advantage of the use of inducible host cell promoters over constitutive host cell promoters can be seen. In growing a culture of a recombinant microbe in a fermentor, it is desirable to allow the recombinant microbe to replicate as rapidly as possible to reach maximum cell density as quickly as possible. Expression of RNA polymerase and the protein-encoding gene during the growth phase of a fermentation would retard the rate of growth of the recombinant microbe by diverting protein production away from host proteins. Driving expression of the heterologous RNA polymerase by an inducible promoter allows the operator to activate expression of RNA polymerase and, subsequently, the protein-encoding gene by addition of the inducer molecule during the stationary phase, the time after the recombinant microbe has reached maximum cell density. The more rapid arrival of the cell density of the recombinant microbe at the maximum cell density brings about production of higher levels of heterologous proteins than a constitutive expression system would produce with a comparable investment of resources and time.

Using either an inducible or a constitutive microbial promoter, the heterologous RNA polymerase gene can be expressed by the recombinant microbe. Expression of the heterologous RNA polymerase gene requires addition of the inducer molecule to the fermentation vessel at a level sufficient to induce transcription from substantially all copies of the inducible microbial promoter. Transcription of the heterologous RNA polymerase gene and subsequent translation of the heterologous RNA polymerase gene mRNA lead to production of the heterologous RNA polymerase. The heterologous RNA polymerase then recognizes copies of the heterologous promoter found on DNA constructs in the same recombinant microbe, and transcribes the protein-encoding gene. Subsequent translation of the protein-encoding gene mRNA produces target gene product.

Techniques for fermentation of microbes are widely known to those of skill in the art, and any such known techniques can be used in the present invention. Techniques for the culturing of non-microbial host cells are also widely known to those of skill in the art, and any such known techniques can also be used in the present invention.

Purification

In embodiments wherein the host cell is a microbe, after the fermentation has reached its conclusion, the microbes containing target gene product are harvested by techniques widely known to those of skill in the art. Microbes and media are removed from the fermentor and the microbes are separated from the media by a known technique, such as centrifugation.

The target gene product can then be purified from the harvested microbes by techniques that will be specific to each target gene product but that will be known to those of skill in the art of purification of the target gene product.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The Zea mays plastid RRN (ZMRRN) promoter was constructed by Midland Certified Reagent Company, Midland, Tex., USA. The sequence of the ZMRRN promoter is given as SEQ ID NO:1. The ZMRRN promoter was synthesized as a double stranded DNA (dsDNA) with overlapping ends compatible with FsiI and AscI sites.

Plasmid pXT225 was digested with FsiI and AscI, and the ZMRRN promoter was ligated into the cut pXT225, by techniques widely known to those skilled in the art. A reporter gene was then inserted into the ZMRRN-containing pXT225 at a position wherein the reporter gene was operably linked with the ZMRRN promoter.

Transformation of E. coli with the ZMRRN/reporter gene construct in pXT225 was then performed by techniques well known in the art. Isolation of mRNA followed by Northern blotting with probes complementary to the reporter gene revealed no reporter gene transcription took place in E. coli in the absence of a plant plastid polymerase.

Further, a gene encoding a plant plastid polymerase can be introduced into an E. coli containing the ZMRRN/reporter gene construct by transformation. The gene encoding the plant plastid polymerase can be chosen to be compatible with pXT225. Isolation of mRNA followed by Northern blotting with probes complementary to the reporter gene can reveal reporter gene transcription taking place in the presence of the plant plastid polymerase.

EXAMPLE 2

A protein-encoding gene encoding bovine somatotropin (bST) can be placed under control of the ZMRRN promoter. The bST gene can be modified to have a codon usage more closely resembling that of E. coli, as well as have convenient restriction endonuclease sites for ease of reconstruction of the gene. The bST gene can also have all introns removed. The protein sequence of bST can be changed by retaining the N-terminal Met, which cannot be cleaved in E. coli. The construct of the bST gene, operably linked to the ZMRRN promoter, can be introduced into an appropriate vector.

The single-subunit, Arabidopsis plastid RNA polymerase gene can be placed under control of a recA promoter of E. coli. As for the bST gene, the nucleotide sequence of the Arabidopsis plastid RRN RNA polymerase gene can be altered to enhance expression, but the amino acid sequence of the RNA polymerase will not be altered except for the possible retention of the N-terminal Met. The construct of the Arabidopsis plastid RRN RNA polymerase gene, operably linked to the recA promoter of E. coli, can be introduced into a second appropriate vector, compatible with the first. Both the first and second vector can each contain a constitutively-expressed marker gene. The two marker genes must be different.

A strain of E. coli can be transformed with the two vectors. A culture of putative transformant E. coli can be plated onto an appropriate agar-containing medium containing two antibiotics, each one corresponding to one of the two marker genes. Bacteria that do not contain both plasmids will be susceptible to either or both of the antibiotics. Only bacteria that contain both plasmids can survive. A colony can then be picked from the plate and grown up in test tubes containing an appropriate medium and the two antibiotics. After several rounds of scaling up, the culture can be added to a fermentor containing an appropriate medium and the two antibiotics. To this point, the culture will not have been exposed to nalidixic acid, the inducer of the recA promoter.

The culture of E. coli containing the bST and plastid RNA polymerase genes can then replicate until the fermentor contains the maximum possible cell density. The maximum possible cell density will vary with the richness of the medium, the temperature of the fermentor vessel, aeration of the medium, features of the E. coli strain, and other features. Once the fermentor contains the maximum possible cell density of E. coli containing the bST and plastid RNA polymerase genes, expression of the plastid RNA polymerase can be induced by addition of nalidixic acid to the fermentor. Nalidixic acid is a known activator of expression of genes under control of the recA promoter. The plastid RNA polymerase can be expressed, and thereafter can associate with the plastid promoter operably linked with the bST gene to generate transcripts of the bST gene. The bST transcripts can then dock to bacterial ribosomes, and bST protein can be produced.

After some length of time, typically 2–12 hours, has elapsed, the culture of E. coli now containing bST protein can be extracted from the fermentor to yield a cell paste. The cell paste can then be lysed by known techniques, for example freeze/thaw cycles, lysozyme-treatment, or French press. The bST protein can be purified from the bacterial DNA and protein fractions by techniques widely known to those skilled in the art.

All of the compositions and methods disclosed and claimed herein can be made and executed without undue experimentation in light of the present disclosure. While the compositions and methods of this invention have been described in terms of preferred embodiments, it will be apparent to those of skill in the art that variations can be applied to the compositions and methods and in the steps or in the sequence of steps of the method described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Hajdukiewicz et al., *EMBO J* (1997) 16, 4041–4048
Binder et al., *Plant Mol. Biol.* (1996) 32, 303–314
Makrides, *Microbiological Reviews*, (1996), 60, 512–538

What is claimed is:

1. A vector system comprising:
   a protein-encoding gene;
   a plant organellar genomic promoter operably linked to said protein-encoding gene;
   a gene encoding an RNA polymerase; and
   a second promoter operably linked to said gene encoding an RNA polymerase;
   wherein said RNA polymerase recognizes said plant organellar genomic promoter.

2. The vector system of claim 1, wherein said plant organellar genomic promoter is not recognized by an RNA polymerase normally found in said host cell.

3. The vector system of claim 2, wherein:
   said plant organellar genomic promoter is a plastid promoter or a plant mitochondrial promoter; and
   said RNA polymerase is a plant RNA polymerase.

4. The vector system of claim 3, wherein:
   said plant organellar genomic promoter is the ZMRRN, SOYRRN, or NTRRN promoter;
   said plant RNA polymerase is the Arabidopsis plastid RNA polymerase;
   said second promoter is an inducible promoter which controls gene transcription in the presence of a corresponding inducer; and
   said inducible promoter is selected from the group consisting of trp, tac, lac, ara, recA, lpp, phoA, proU, cst-1, tetA, cadA, nar, trc, lpp-lac, Psyn, cspA, Vhb, λPr, and λPl.

5. A transformed host cell useful for expressing a protein-encoding gene, said transformed host cell comprising:
   a protein-encoding gene;
   a plant organellar genomic promoter operably linked to said protein-encoding gene, wherein the plant organellar genomic promoter is heterologous with respect to the protein-encoding gene;
   a gene encoding an RNA polymerase, wherein the gene encoding the RNA polymerase is heterologous with respect to a non-transformed host cell of the same species; and a second promoter operably linked to said gene encoding an RNA polymerase;

wherein said RNA polymerase recognizes said plant organellar genomic promoter.

6. The host cell of claim 5, wherein said plant organellar genomic promoter is not recognized by an RNA polymerase normally found in the host cell.

7. The host cell of claim 6, wherein:

said plant organellar genomic promoter is a plastid promoter or a plant mitochondrial promoter; and said RNA polymerase is a plant RNA polymerase.

8. The host cell of claim 7, wherein said host cell is an animal cell.

9. The host cell of claim 7, wherein said host cell is a plant cell.

10. The host cell of claim 7, wherein said host cell is a microbe.

11. The host cell of claim 10, wherein said microbe is selected from the group consisting of Escherichia, Bacillus, Pseudomonas, Chlamydomonas and Saccharomyces.

12. The host cell of claim 10, wherein said microbe is a bacterium.

13. The host cell of claim 12, wherein:

said bacterium is *Escherichia coli;* said plant organellar genomic promoter is the ZMRRN, SOYRRN, or NTRRN promoter;

said plant RNA polymerase is the Arabidopsis plastid RNA polymerase;

said second promoter is an inducible promoter which controls gene transcription in the presence of a corresponding inducer; and said inducible promoter is selected from the group consisting of trp, tac, lac, ara, recA, lpp, phoA, proU, cst-1, tetA, cadA, nar, trc, lpp-lac, Psyn, cspA, Vhb, λPr, and λPl.

14. A method for producing a host cell expressing a protein-encoding gene, the method comprising introducing a vector system into said host cell to form a recombinant host cell, said vector system comprising:

a protein-encoding gene;

a plant organellar genomic promoter operably linked to said protein-encoding gene;

a gene encoding an RNA polymerase; and a second promoter operably linked to said gene encoding an RNA polymerase;

wherein said RNA polymerase recognizes said plant organellar genomic promoter.

15. The method of claim 14, wherein said plant organellar genomic promoter is not recognized by an RNA polymerase normally found in the host cell.

16. A method for expressing a protein-encoding gene in a host cell, the method comprising the steps of:

introducing a vector system into said host cell to form a recombinant host cell, said vector system comprising:

a protein-encoding gene;

a plant organellar genomic promoter operably linked to said protein-encoding gene;

a gene encoding an RNA polymerase; and a second promoter operably linked to said gene encoding an RNA polymerase; and growing said recombinant host cell;

wherein said RNA polymerase recognizes said plant organellar genomic promoter.

17. The method of claim 16, wherein said plant organellar genomic promoter is not recognized by an RNA polymerase normally found in the host cell.

18. The method of claim 17, wherein:

said plant organellar genomic promoter is a plastid promoter or a plant mitochondrial promoter; and said RNA polymerase is a plant RNA polymerase.

19. The method of claim 18, wherein said host cell is an animal cell.

20. The method of claim 18, wherein said host cell is a plant cell.

21. The method of claim 18, wherein said host cell is a microbe.

22. The method of claim 21, wherein said microbe is selected from the group consisting of Escherichia, Bacillus, Pseudomonas, Chlamydomonas and Saccharomyces.

23. The method of claim 21, wherein said microbe is a bacterium.

24. The method of claim 23, further comprising a step of adding an inducer after said growing step, wherein:

said bacterium is *Escherichia coli;* said plant organellar genomic promoter is the ZMRRN, SOYRRN, or NTRRN promoter;

said plant RNA polymerase is the Arabidopsis plastid RNA polymerase;

said second promoter is an inducible promoter that controls gene transcription in the presence of a corresponding inducer;

said inducible promoter is selected from the group consisting trp, tac, lac, ara, recA, lpp, phoA, proU, cst-1, teta, cadA, nar, trc, lpp-lac, Psyn, cspA, Vhb, λPr, and λPl; and said step of growing said recombinant host cell is performed in the absence of said inducer.

25. The method of claim 24, wherein:

said protein-encoding gene is a bovine somatotropin gene;

said inducible promoter is recA; and said inducer is nalidixic acid.

* * * * *

SEQUENCE LISTING

<160> NUMBER OF SEQ ID NOS: 3

<210> SEQ ID NO 1
<211> LENGTH: 185
<212> TYPE: DNA
<213> ORGANISM: Zea mays

<400> SEQUENCE: 1

| | | | | | | |
|---|---|---|---|---|---|---|
| actcccccac | cacgatcgaa | cgggaatgga | taggaggctt | gtgggattga | cgtgataggg | 60 |
| tagggttggc | tatactgctg | gtggcgaact | ccaggctaat | aatctgaagc | gcttggatac | 120 |
| aagttatcct | tggaaggaaa | gacaattccg | gatcttaatt | caagagttgt | agggagggat | 180 |
| ccatg | | | | | | 185 |

<210> SEQ ID NO 2
<211> LENGTH: 176
<212> TYPE: DNA
<213> ORGANISM: Nicotiana tabacum
<220> FEATURE:
<221> NAME/KEY: unsure
<222> LOCATION: (44)
<223> OTHER INFORMATION: n=a, c, t, or g

<400> SEQUENCE: 2

| | | | | | | |
|---|---|---|---|---|---|---|
| tgatcgaata | ataattgaga | atggataaga | ggctcgtggg | attnacacga | ggggtggggg | 60 |
| ggctatattt | ctgggagcga | actccagtcg | aatatgaagc | gcctggatac | aagttatccc | 120 |
| ttggaataga | agacaattcc | ggatcttaat | tcaagagttg | tagggaggga | tccatg | 176 |

<210> SEQ ID NO 3
<211> LENGTH: 184
<212> TYPE: DNA
<213> ORGANISM: Nicotiana tabacum

<400> SEQUENCE: 3

| | | | | | | |
|---|---|---|---|---|---|---|
| tgctcccccg | ccgtcgttca | atgagaatgg | ataagaggct | cgtgggattg | acgtgagggg | 60 |
| gcagggatgg | ctatatttct | gggagcgaac | tccgggcgaa | tatgaagcgc | atggatacaa | 120 |
| gttatgcctt | ggaatgaaag | acaattccga | atcttaattc | aagagttgta | gggagggatc | 180 |
| catg | | | | | | 184 |